United States Patent
Lee et al.

(10) Patent No.: US 6,558,377 B2
(45) Date of Patent: May 6, 2003

(54) EMBOLIC MATERIAL DETACHMENT DETECTION SYSTEM AND METHOD AND ASSEMBLY FOR EMBOLIC TREATMENTS

(75) Inventors: Kyu-Ho Lee, Hyundai Villa 7-201, 172 Sangil-dong, Gangdong-gu, Seoul 134-090 (KR); Yong-Churl Kim, Daejeon-si (KR)

(73) Assignee: Kyu-Ho Lee, Seoul (KR)

( * ) Notice: Subject to any disclaimer, the term of this patent is extended or adjusted under 35 U.S.C. 154(b) by 53 days.

(21) Appl. No.: 09/757,408

(22) Filed: Jan. 9, 2001

(65) Prior Publication Data

US 2002/0029035 A1 Mar. 7, 2002

(30) Foreign Application Priority Data

Jul. 26, 2000 (KR) .............................................. 00-42929

(51) Int. Cl.$^7$ ............................................... A61B 18/04
(52) U.S. Cl. ............................. 606/32; 606/41; 600/381
(58) Field of Search ............................. 606/28, 32, 41, 606/45, 108, 200; 604/27, 28, 57, 59, 60, 93.01, 171, 907; 600/372–381

(56) References Cited

U.S. PATENT DOCUMENTS

| | | |
|---|---|---|
| 5,522,836 A | 6/1996 | Palermo |
| 5,624,449 A | 4/1997 | Pham et al. |
| 5,643,254 A | 7/1997 | Scheldrup et al. |
| 5,725,534 A | 3/1998 | Rasmussen et al. |
| 6,013,084 A | 1/2000 | Ken et al. |
| 6,059,779 A * | 5/2000 | Mills ........................... 600/373 |
| 6,123,714 A * | 9/2000 | Gia et al. ....................... 606/1 |
| 6,375,669 B1 * | 4/2002 | Rosenbluth et al. ......... 606/108 |
| 6,397,850 B1 * | 6/2002 | Scheldrup et al. .......... 128/899 |

* cited by examiner

*Primary Examiner*—Roy D. Gibson
(74) *Attorney, Agent, or Firm*—Gibbons, Del Deo, Dolan, Griffinger & Vecchione

(57) ABSTRACT

A system and method for determining the detachment of an embolic material using a single power supply are disclosed, wherein the determination is made by applying a DC power to an assembly with an embolic material, a sacrificial link and a guiding wire which are serially connected and repeatedly measuring a voltage and current between the assembly and the ground for a plurality of cycles and a plurality of times in each cycle; computing an average of the measured voltages and an average of measured currents; and determining the detachment of the embolic material from the guiding wire based on a change in impedance between the guiding wire and the ground, wherein the change is detected using the present average of the measured voltages, the present average of the measured currents and a previous average voltage which is previously measured for a plurality of times.

14 Claims, 13 Drawing Sheets

EMBOLIC MATERIAL DETACHMENT DETECTION SYSTEM AND METHOD AND ASSEMBLY FOR EMBOLIC TREATMENTS

FIELD OF THE INVENTION

The present invention relates to an apparatus and method for filling a target site in a living being with an embolic material to occlude the site; and, more particularly, to an apparatus and method for automatically notifying an operator of the instant the embolic material is detached from a guiding member by electrolytic action.

BACKGROUND OF THE INVENTION

There is an operative treatment of treating vascular malformations such as a cerebral aneurysm, which includes the processes of putting a patient under general anesthesia to craniotomy, exposing the cerebral aneurysm in the patient using an operating microscope and a microsurgical unit, and clipping a cervical portion of the cerebral aneurysm with a particular metallic clip. However, such a treatment suffers from drawbacks that it still involves a considerable hazard and a prolonged operating time, which, in turn, may cause serious sequelae.

In an alternative treatment, a Minimal Invasive Treatment (MIT), which employs a technique disclosed in U.S. Pat. No. 5,122,136 issued to Guglielmi et al, and U.S. Pat. Nos.4, 884,579 and U.S. Pat. No. 4,739,768 issued to Engelson, is utilizing. The MIT Treatment inserts an embolic material within vascular malformations such as a cerebral aneurysm through the use of a micro catheter and a guiding wire under fluoroscopy to occlude the vascular malformations. In contrast with the craniotomy treatment previously explained, the MIT treatment has merits that it is possible to operate under a slight anesthesia with a short operation time, to thereby minimize sequelae and also lower an operation cost.

An embolic material mainly utilized in the MIT treatment includes a metallic coil. The metallic coil is disclosed in, for example, U.S. Pat. Nos. 5,354,295, 5,669,905 and 6,066,133 and Japanese Patent Nos. 10-057385, 11-047138 and 11-076249. In the following, the metallic coil cited in U.S. Pat. No. 5,669,905 will be described.

FIG. 1 is a pictorial view of a metallic embolic coil used in the conventional MIT treatment.

As shown in FIG. 1, a guiding wire assembly 100 typically includes a stainless steel-based guiding wire 1 and a coil-shaped embolic material 8, the guiding wire 1 being tapered its distal end and the embolic material 8 being connected with the distal end of the guiding wire 1 by a micro welding. The embolic material 8 is made of a radiopaque material including Platinum, Tungsten, Iridium or these alloys, and has welded portions 6 and 7 at its both ends. The welded portions 6 and 7 are made of platinum that acts as a marker under fluoroscopy.

A surface of the guiding wire 1 is coated with an insulating material such as Teflon, with the exception of a proximal end 5 acting as a sacrificial link to be connected with the welded portion 6 of the embolic material 8. The sacrificial link 5 is made of an electrically conducting material such as stainless steel, which is a portion to be detached from the guiding wire 1 by electrolytic disintegration. The guiding wire 1 is coupled with the welded portion 6 of the embolic material 8 via the sacrificial 5, which is interposed in a sleeve 2 and a plug 3 with inserted within an internal coil 4. The internal coil 4 is designed to provide column strength to the guiding wire 1, without a bad influence for a flexibility of the tapered portion in the guiding wire 1. As shown in FIG. 1, the embolic material 8 has been designed its shape changed into a coil form when it is gradually withdrawn from a micro catheter 7, to thereby allow the embolic material to adapt to the shape of the vascular malformation.

FIG. 2 is a pictorial view illustrating insertion and detachment processes of the embolic material 8 in the prior art.

Typically, the insertion of the embolic material 8 in a vascular malformation 11 is performed using fluoroscope under local anesthesia. Specifically, as shown in FIG. 2A, an operator guides a micro catheter 10 to near neck 12 of the vascular malformation 11 in a living being or a patient. After that, the operator inserts the guiding wire 1 attached the embolic material 8 on its distal end into the micro catheter 10, and gently push the guiding wire 1 using the fluoroscope at least until the sacrificial link 5 is exposed beyond the distal end of the micro catheter 10.

In an ensuing step, an electrical loop is formed wherein a positive electrode of a power supply 13 is attached to the proximal end of the guiding wire 1 and a negative electrode is placed in electrical contact with the skin of the patient. Thereafter, the power supply 13 is turned on to allow a DC power with AC superposition to be applied to the embolic material 8 through the sacrificial link 5 of the guiding wire 1. As a result of the above process, the embolic material 8 is detached from the guiding wire 1 by electrolysis as shown in FIG. 2B. Next, the guiding wire 1 and the micro catheter 10 are withdrawn from the vascular malformation 11.

FIG. 3 shows a schematic block diagram of the prior art apparatus of detecting the detachment of the embolic material from the guiding wire.

The prior art apparatus 200 includes a constant current source 16, a circuit 18 for detecting the detachment of the embolic material and a microprocessor 19. The constant current source 16 provides a constant current to the patient 17, which includes an operational amplifier (OP Amp) 16a and a DC feedback loop 16b. The OP Amp 16a will oscillate in approximately 30 kHz at amplitude of several hundred milli-volts due to a lagging error correction signal (out-of-phase feedback). That is, the OP Amp 16a provides a DC current with AC superposition. The amplitude of such AC signal is dependent on bandwidth characteristics of the OP Amp 16a, AC impedance of the stainless steel and the embolic material 8, and the patient's body. The DC constant current flowing out of the OP Amp 16a flows through the sacrificial link 5 of the guiding wire 1 to the embolic material 8.

Although the sacrificial link 5 and the embolic material 8 are physically connected in series, immersion of them in an electrolytic solution forms two parallel DC current paths each of that is grounded through the body of the patient 17. Specifically, by ion flow away from the stainless steel-based link 5 during electrolysis, the DC current with AC superposition flowing between the sacrificial link 5 and the embolic material 8 in the vascular malformations 11 is branched as follows. That is, the majority of the DC current (above 99%) flows through the sacrificial link 5 with the remaining (less 1%) flowing through the embolic material 8. Thus, if the embolic material 8 is separated from the link 5 and a portion of the sacrificial link 5 remains attached to the guiding wire 1, the main DC current is fed back to the DC feedback loop 16b of the constant current source 16. The AC current is grounded through the embolic material 8.

As shown in FIG. 3, the DC current with AC superposition is blocked out by a pick-off capacitor (not shown), only the AC signal is fed to the detection circuit 18 for measurement of AC impedance. The detection circuit 18 receives the AC current from the embolic material 8 in the patient 17 to detect whether or not the embolic material 8 is detached. Specifically, the AC current fed to the detection circuit 18 is amplified in an AC signal amplifier 18a and is rectified in an AC-DC rectifier 18b. Then, the rectified DC signal is amplified in a DC level amplifier 18c and sent to the microprocessor 19, wherein the amplified DC level is representative of the amplitude of the AC voltage of the OP Amp 16a.

The microprocessor 19 monitors the level of the amplified DC signal every 50 to 200 milliseconds and constantly averages the signal every specific sample. In this manner, if a sudden DC voltage drop is incurred, the microprocessor 19 determines that the embolic material 8 is detached from the guiding wire 1.

In the prior art, the OP Amp 16a oscillated on its own, which allowed the monitoring of the AC impedance fluctuation by the detection circuit 18. Since, however, there were fluctuations in the self-oscillation signal flowing- from unit to unit, it fails to exactly determine the instant the embolic material is detached. That is to say, a fluctuation in the AC impedance depends on a length of the embolic material and other physical factors, thereby invoking poor detachment detection.

To support this, as shown in FIG. 4, an external AC source 20b is utilized to ensure all units will show the identical response to the fluctuation in the AC impedance. In FIG. 4, the AC source 20b is coupled with a reference input Vref of an OP Amp 20a so as to modulate the output current of the OP Amp 20a (i.e., provide AC superposition on the DC current). A DC current with AC superposition is outputted from the OP Amp 20a and sent to the embolic material 8 through the sacrificial link 5 of the guiding wire 1. As a result, two AC and DC current paths branch as described above with reference to FIG. 3. The DC current with AC superposition from the patient 17 is fed back to an AC & DC feedback loop 20c of a constant current source 20 and fed to the OP Amp 20a.

As stated above, the DC current with AC superposition is blocked out by a pick-off capacitor (not shown), only the AC signal is fed to the detection circuit 21 for measurement of AC impedance fluctuation. In the detection circuit 21, since the amplitude of the AC signal is substantially greater than that of FIG. 3, the DC level amplifier 18c in FIG. 3 is not necessary. As noted, the AC signal is amplified in an AC signal amplifier 21a in the detection circuit 21 and is rectified in an AC-DC rectifier 21b. Then, the rectified DC signal is sent to the microprocessor 19.

In short, the prior art apparatuses previously disclosed detect the detachment of the embolic material using the AC signal. Accordingly, the prior art apparatuses suffer from a drawback that if a fluctuation in the AC impedance depends on a length of the embolic material and other physical factors, it is difficult to exactly detect the detachment instant. In addition, the prior art guiding wire assembly for embolization demands to an additional coil for maintaining the shape of the guiding wire and an additional signal source, thereby rendering the apparatus rather complex and costly. Likewise, although the embolic material in the prior art has been fabricated in platinum, tungsten, gold, iridium or alloy for thrombus in vascular malformations, it would be desirable to effectively enhance the rate of thrombus without any application of high power to the material.

SUMMARY OF THE INVENTION

It is, therefore, an object of the present invention to provide a system and method for exactly determining the instant an embolic material is detached through the use of a single power supply, without any additional circuits.

It is another object of the present invention to provide an assembly for embolization, which includes a simplified guiding member and an embolic material inducing an improved thrombus in vascular malformations.

In accordance with a preferred embodiment of the present invention, there is provided to a system for detecting the detachment of an implant from a guiding member coupled thereto, wherein the implant is guided by the guiding member into a target site in a living being, comprising: means for generating a current; means for supplying the generated current via the guiding member to the implant; means for measuring a voltage and current between the guiding member and the ground for a plurality of cycles, during each of which the voltage and current are measured for a plurality of times; means for computing the average of the measured voltages and the average of measured currents in each cycle; and means for determining the detachment of an implant from the guiding member based on a change in impedance between the guiding member and the ground, wherein the change is detected using the average voltage and average current of the latest cycle of voltage and current measurements, and the average voltage of the previous cycle of voltage and current measurements.

BRIEF DESCRIPTIONS OF THE DRAWINGS

The above and other objects and features of the present invention will become apparent from the following description of preferred embodiments given in conjunction with the accompanying drawings, in which.

Figure 3:
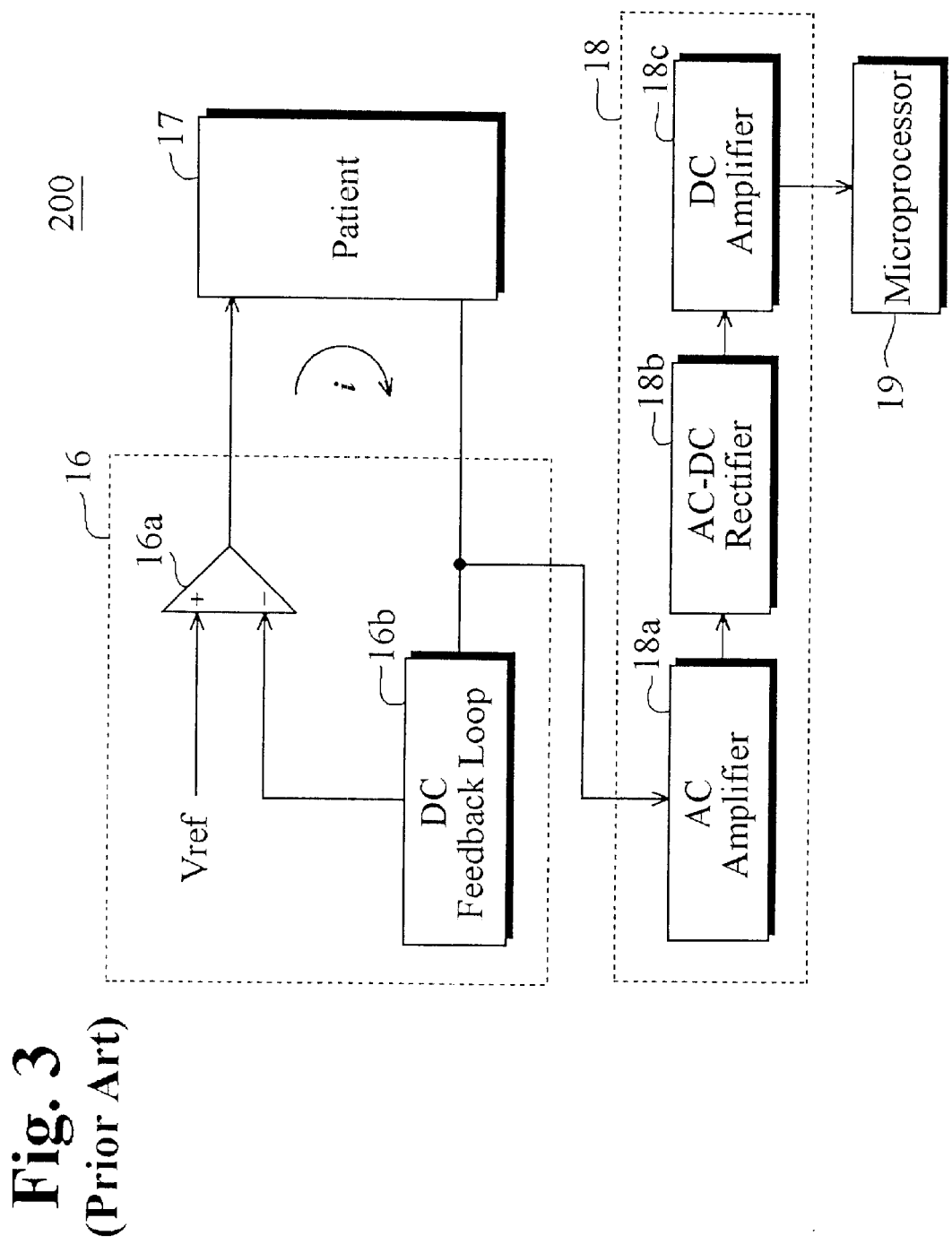
Figure 4:
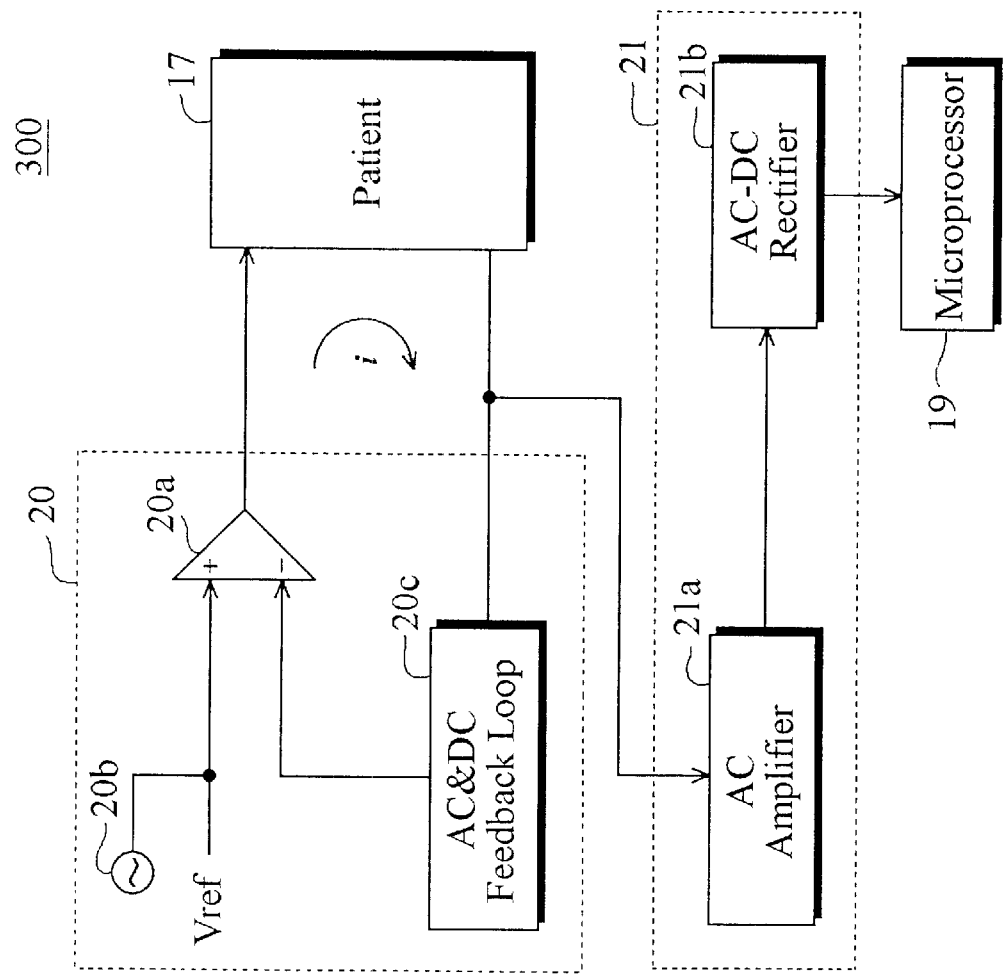
Figure 5A:
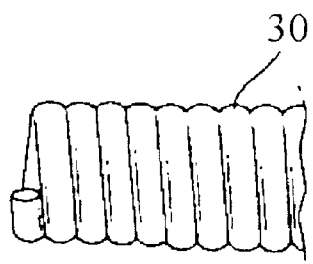
Figure 5B:
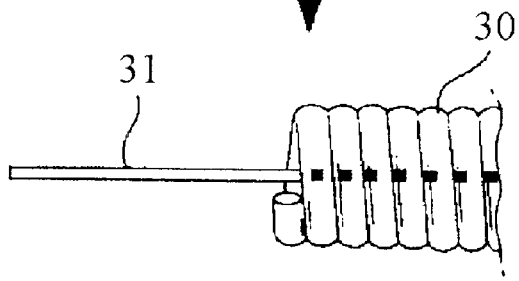
Figure 5C:
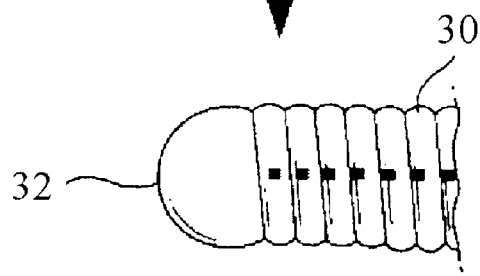

FIG. 3 offers a schematic block diagram of the prior art apparatus of detecting the detachment of the embolic material from the guiding wire;

FIG. 4 depicts a schematic block diagram of the prior art apparatus using an external AC source;

FIGS. 5A to 5c are pictorial views of an embolic material in accordance with a preferred embodiment of the present invention, respectively.

Figure 6A:
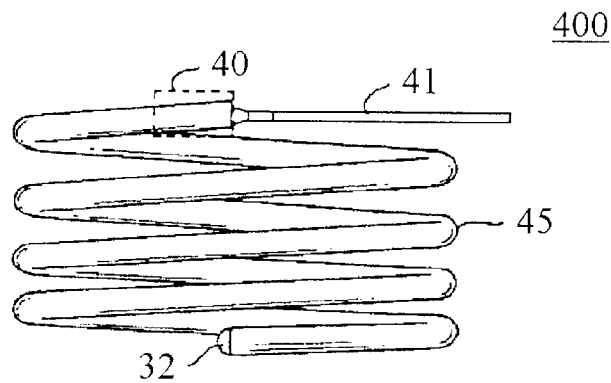
Figure 6B:
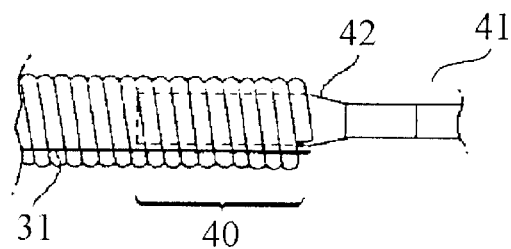
Figure 6C:
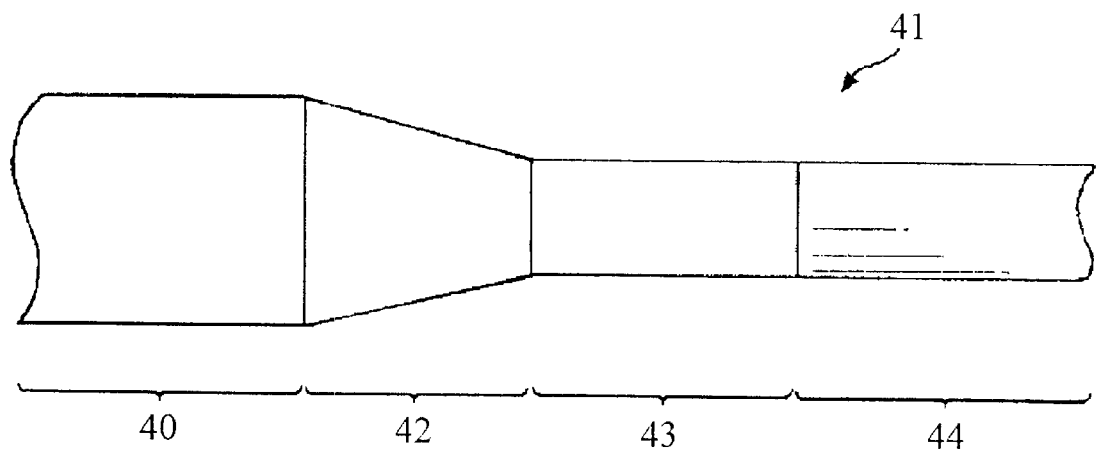
Figure 7A:
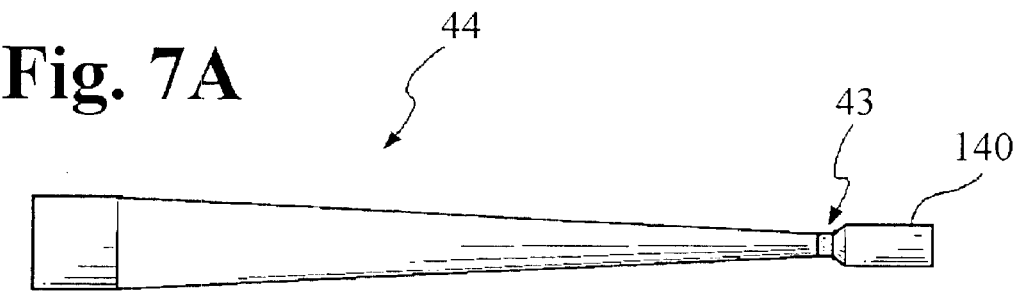
Figure 7B:
Figure 7C:
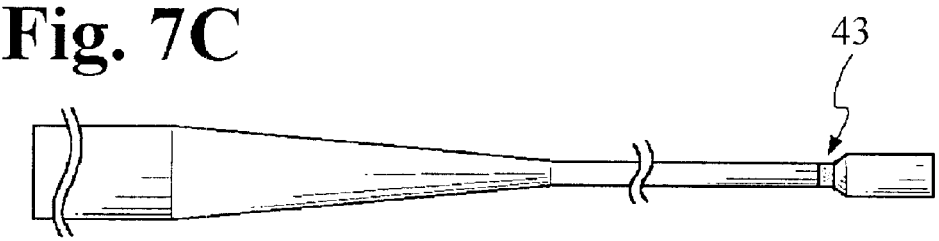
Figure 7D:
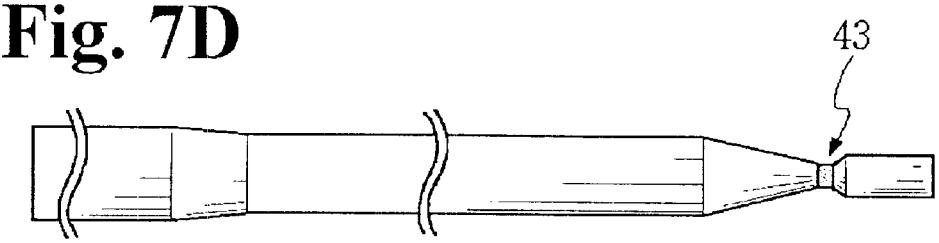
Figure 7E:
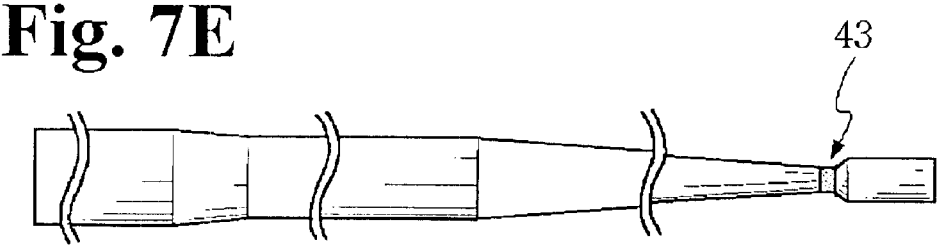

FIGS. 6A to 6c represent pictorial views of an assembly for embolization in which the embolic material having the platinum-based wire therein is coupled with a guiding wire, in accordance with the present invention, respectively.

Figure 8:
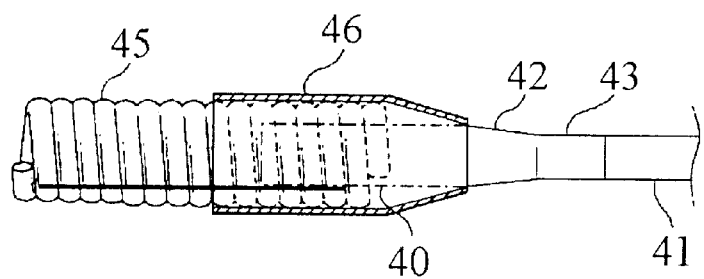
Figure 9:
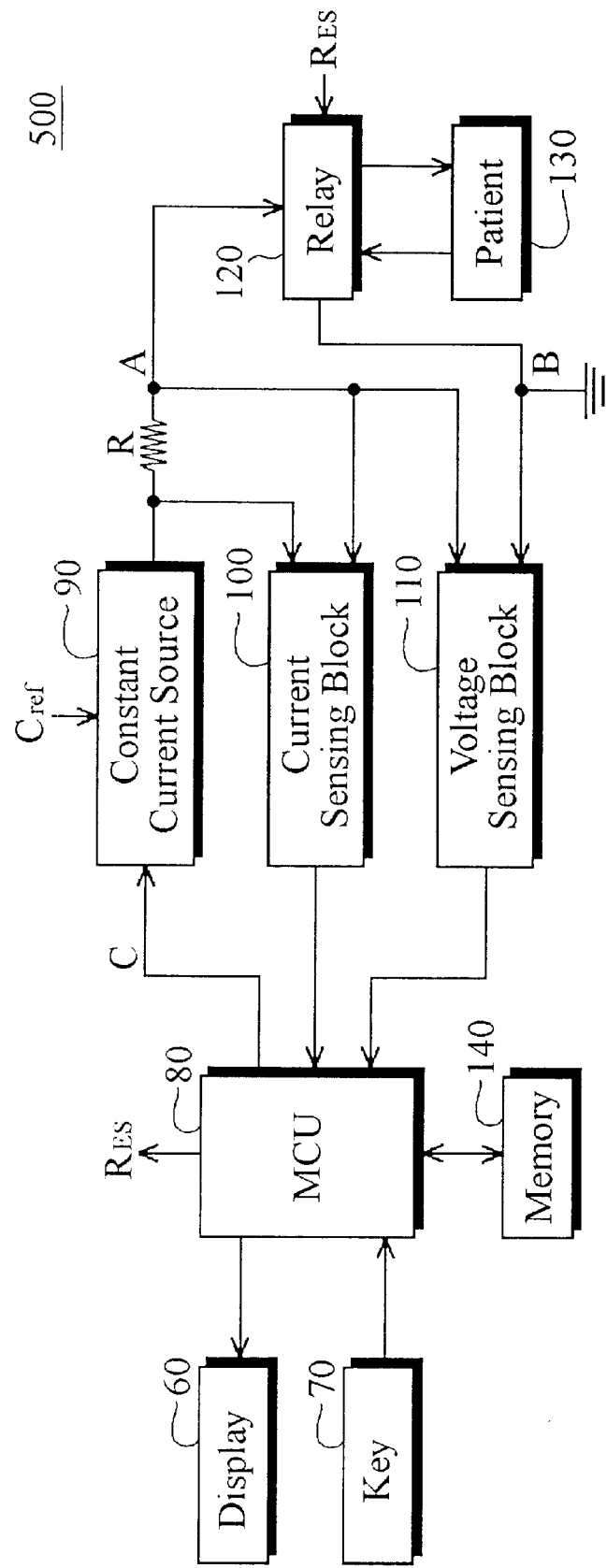

FIGS. 7A to 7E exhibit pictorial views of various guiding wires in accordance with a preferred embodiment of the present invention, respectively;

FIG. 8 is a micro-envelope surrounding a portion at which a micro-welded portion and the embolic material are coupled;

FIG. 9 provides a schematic block diagram of an embolic material detachment detecting system in accordance with another preferred embodiment of the present invention.

Figure 10:
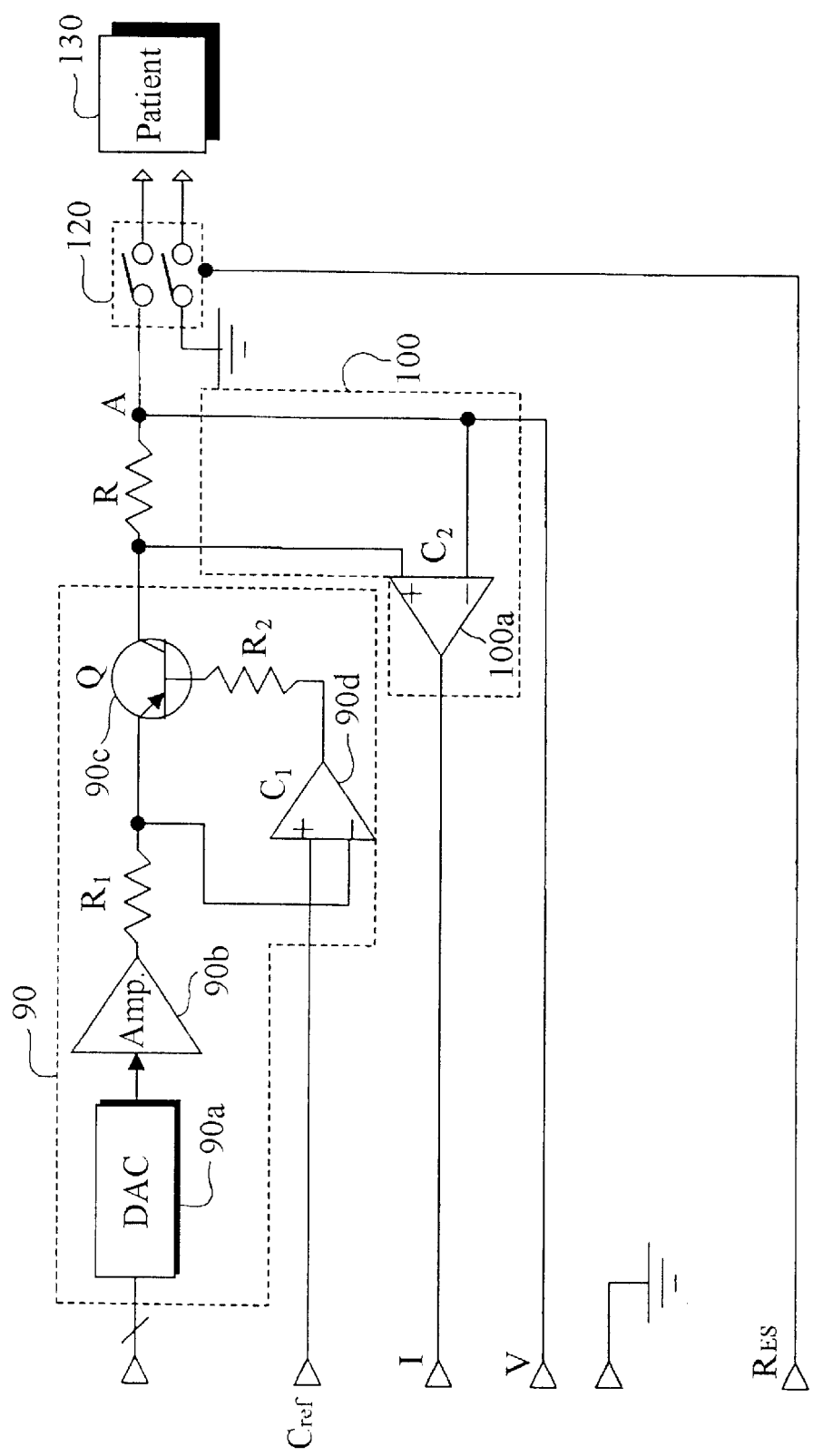
Figure 11:
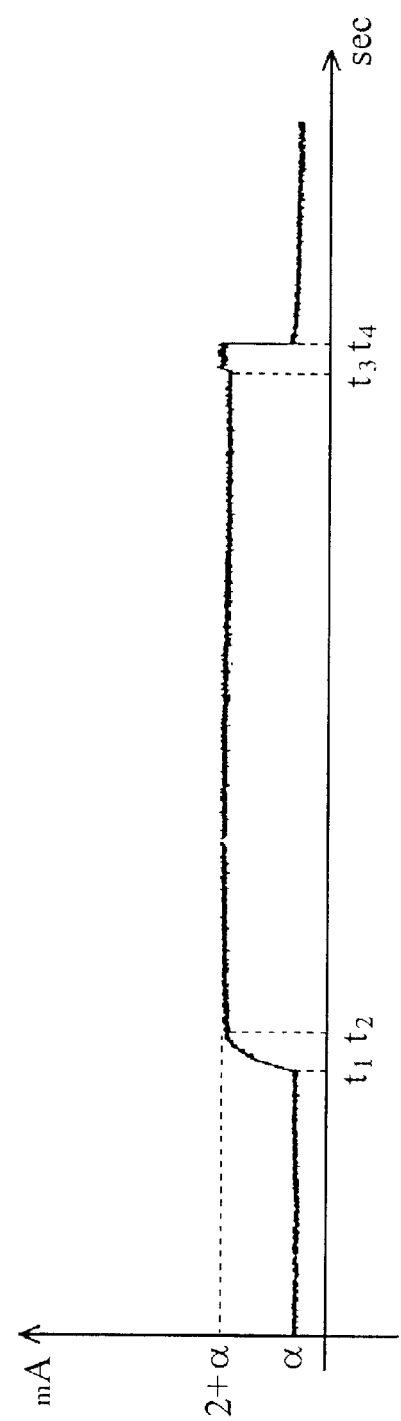
Figure 12:
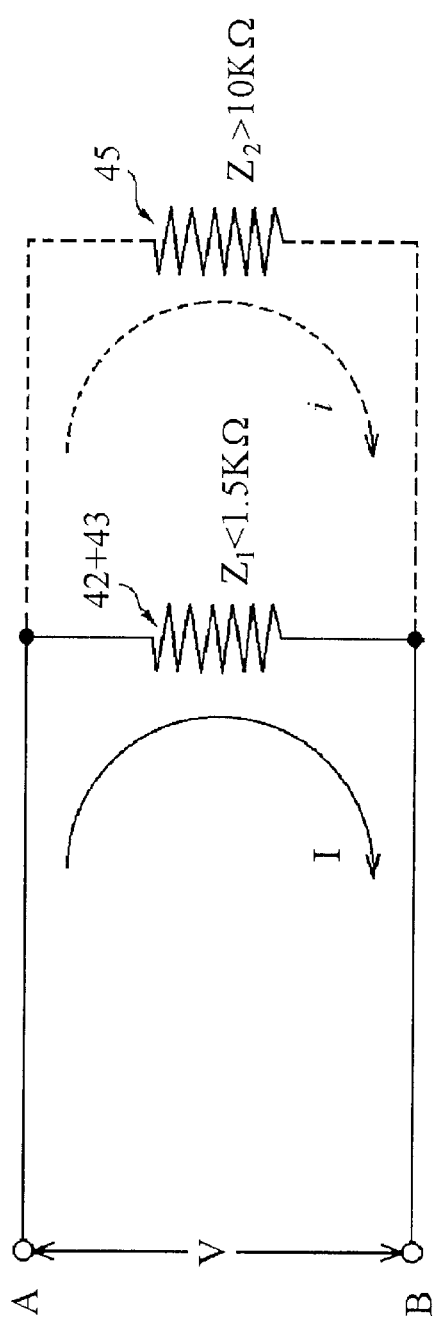
Figure 13:
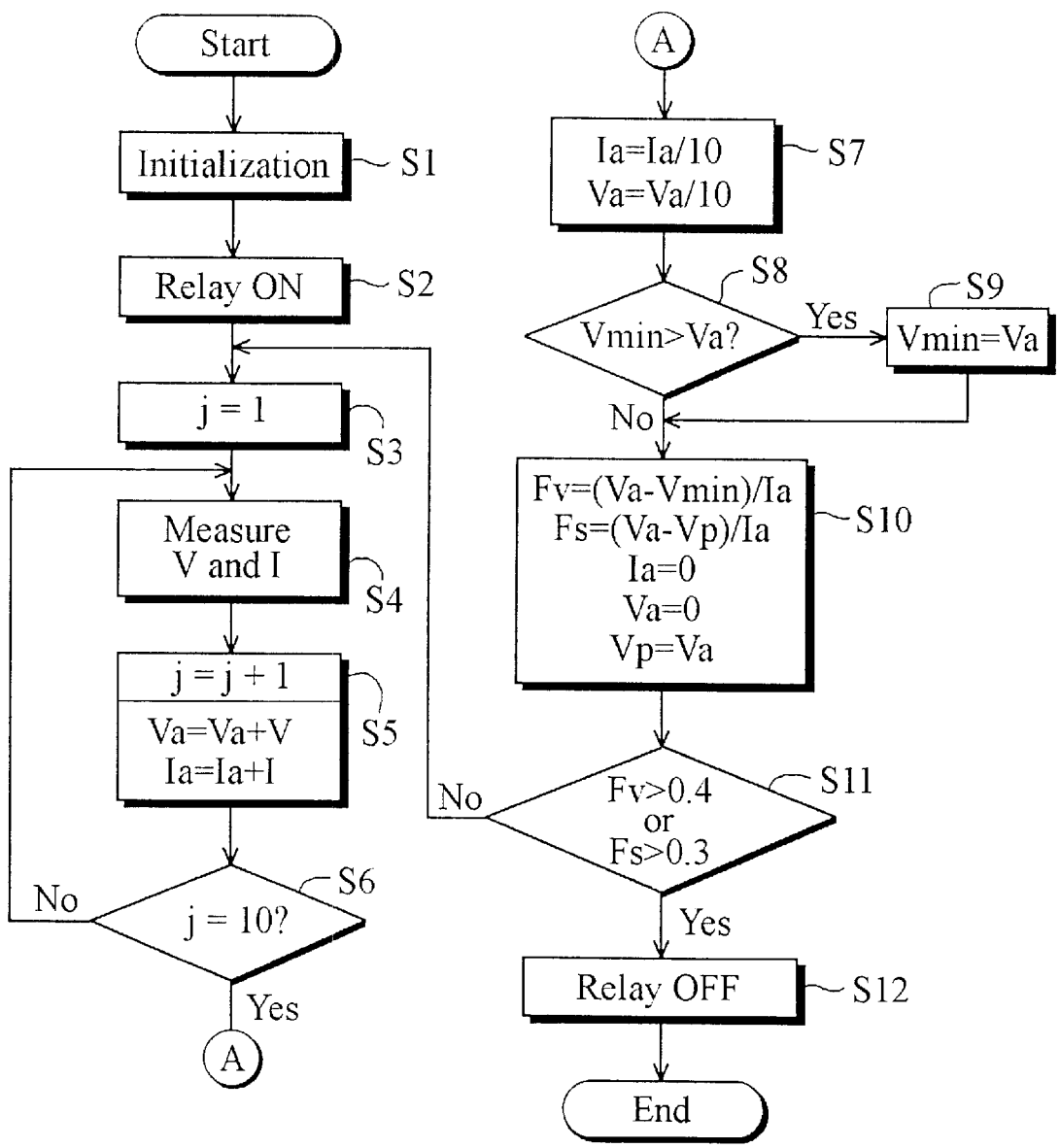
Figure 14:
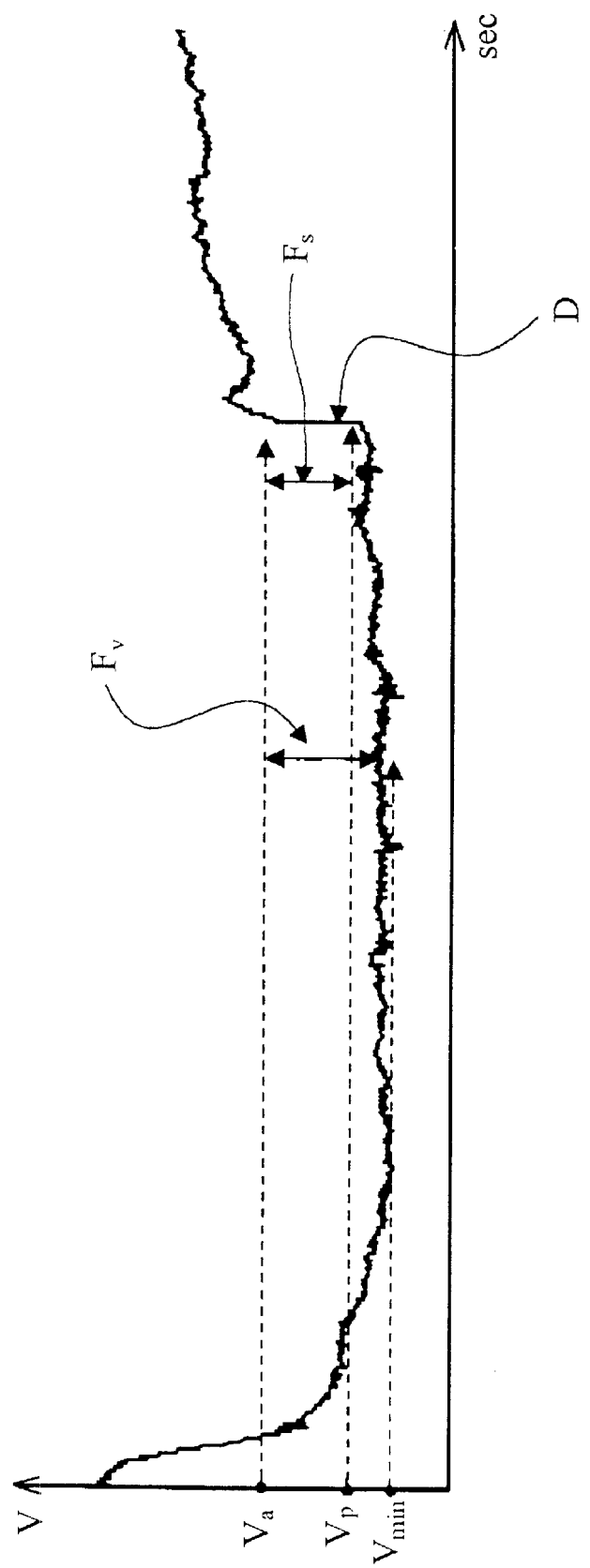
Figure 15A:
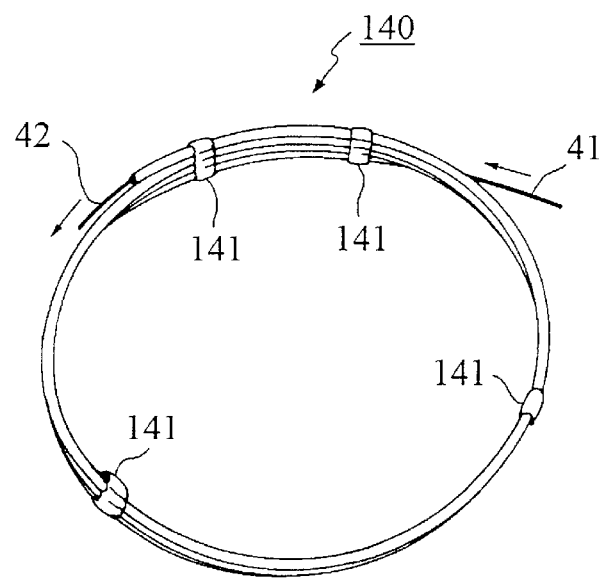
Figure 15B:
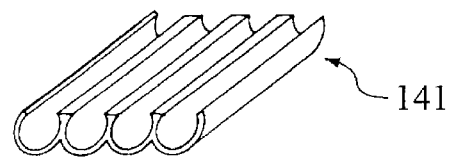
Figure 15C:
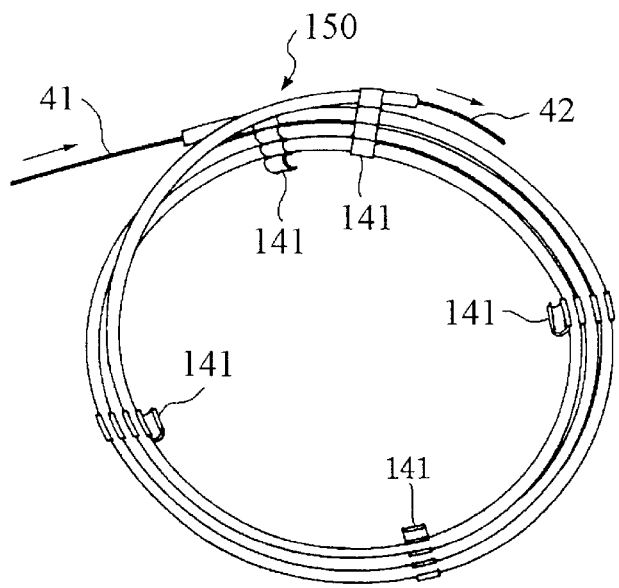

FIG. 10 denotes a detailed block diagram of the constant current source, the current-sensing block and the voltage-sensing block shown in FIG. 9;

FIG. 11 designates a change in current in a sacrificial link during electrolysis;

FIG. 12 illustrates current paths flowing through the sacrificial link and the embolic material, during the application of the current to the embolic material;

FIG. 13 is a flow chart that will be used to describe a method for detecting the detachment of an embolic material, in accordance with still another preferred embodiment of the present invention;

FIG. 14 presents a graphical representation illustrating a fluctuation in voltage in the sacrificial link during electrolysis; and FIGS. 15A to 15C are various type tubes used in keeping therein an assembly for embolization with the embolic material and the guiding wire, in accordance with a preferred embodiment of the present invention.

DETAILED DESCRIPTION OF THE PRESENT INVENTION

Referring to FIGS. 5A to 5c, there are pictorial views of an embolic material in accordance with a preferred embodiment of the present invention.

As shown in FIG. 5A, a primary embolic material 30 is fabricated by forming tungsten or iridium alloy wires with the main part of platinum, in a coil fashion for example. In this case, a diameter of the wire is 25–75 μm and the inner diameter of the primary embolic material 30 (hereinafter called an embolic coil 30) is e.g., 100–150 μm. In this case, the mixture ratio of platinum and iridium may be preferably 90 to 10 or 85 to 15; and that of platinum and tungsten may be preferably 92 to 8.

As shown in FIG. 5B, a pure platinum-based wire 31 having 15 μm in diameter is inserted into the primary embolic coil 30. After that, by melting the platinum-based wire 31 at its one end of the primary embolic coil 30, a circle-like welded portion 32 is formed as presented in FIG. 5c. The welded portion 32 functions as a marker during insertion of the embolic material into a target site in a living being or an organism in fluoroscopy. The primary embolic coil 30 formed thus is modified in a further coil fashion to allow it to be adaptively transformed to a shape of vascular malformation, as shown in FIG. 6. In FIG. 6, a secondary embolic coil 45 has a diameter of 2–8 mm and a length of 4–20 cm for example. Although the shape of the secondary embolic coil 45 is of a cylindrical shape, it may be conic or waveform shapes, which can be adaptively transformed responsive to the shape of the vascular malformation. For the purpose of this specification, the secondary embolic coil 45 is hereinafter referred to as an embolic material 45. Heating it in a temperature of approximately 600–800° C., preferably. 640–750° C., for about 30 minutes, under vacuum condition of 1 atmospheric pressure, and then performing a rapid air-cooling may form the embolic material 45.

As is well known, Platinum, Iridium and Tungsten have an excellent conductivity and radiopaque characteristics. In the above, although the tungsten or iridium alloys with the main part of platinum have been used as a source of the embolic material 45, any material with an excellent conductivity, a radiopaque characteristic and a biocompatibility may be used. A major reason why the platinum-based wire 31 is inserted within the embolic material 45 is to: function as a thermoseed during a radio-frequency heating to accelerate the thrombus; increase a column strength of the embolic material 45; and allow it to be not decomposed during electrolysis. In addition, nickel-titanium alloys with superiority in plasticity and flexibility might be allowable to be used, especially in the case of radiofrequency inductive heating for enhancing thrombosis within the aneurysm.

Referring to FIGS. 6A to 6c, there are shown pictorial views of an assembly for embolization in which the embolic material having the platinum-based coil therein is coupled with a guiding wire, in accordance with the present invention.

As shown in FIG. 6A, the proximal end of an embolic material 45 and the distal end of a guiding wire 41 are connected together by inserting the guiding wire approximately 0.2–0.3 mm into the embolic coil. As shown in FIG. 6B, the diameter of the distal end 40 of the guiding wire 41 is slightly less than the internal diameter of the embolic coil. The connection is made by resistive micro-welding. In this case, the condition of the micro-welding is set such that a change in resistance after the micro-welding should be in 0.02 to 0.03 ohm. The micro-welding is performed at a contact surface between the embolic material 45 and the guiding wire 41 without using a welding flux.

Figure 1:
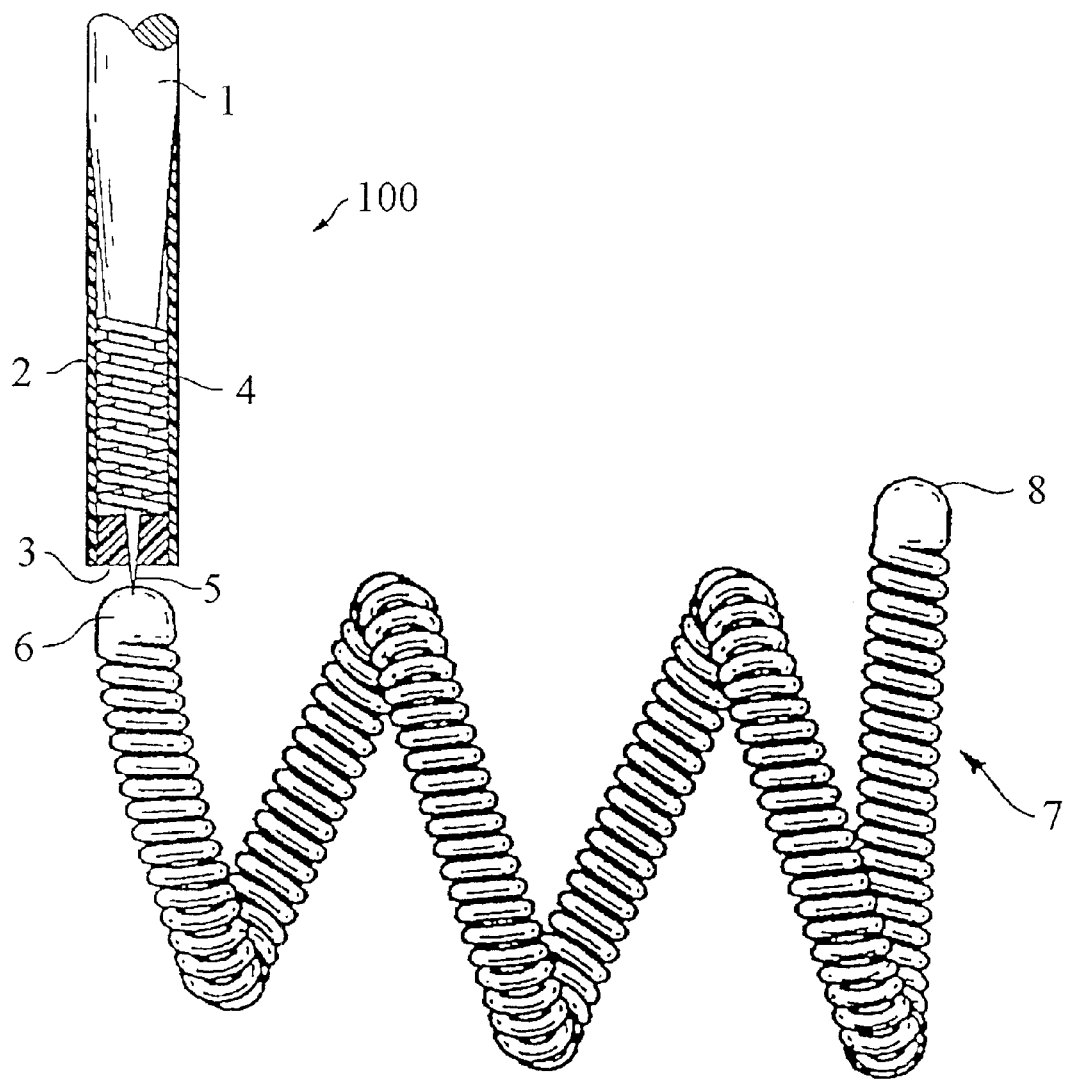
FIG. 1 is a pictorial view of a metallic embolic coil used in the conventional MIT treatment.
Figure 2A:
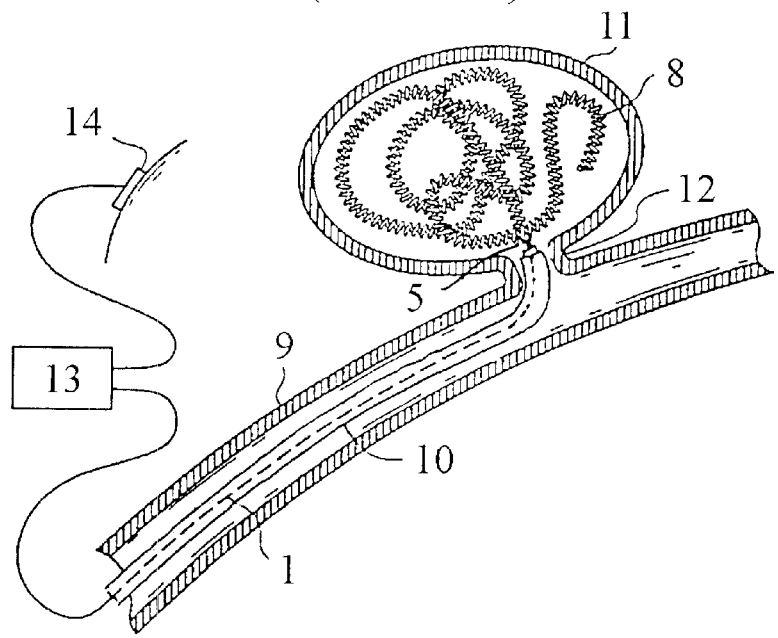
FIGS. 2A and 2B show pictorial views illustrating insertion and detachment processes of the embolic material 8 in the prior art, respectively.
Figure 2B:
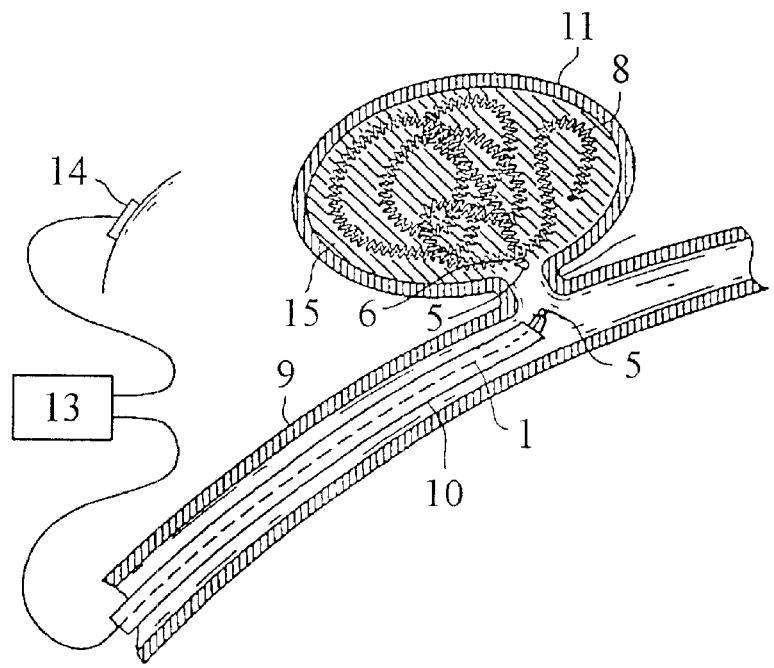

The guiding wire 41, made of an electrically conducting material such as stainless steel, is used to guide the embolic material 45 to a vascular malformation 11 shown in FIG. 2. It consists of the connection portion 40, a tapered portion 42, a sacrificial link 43 and a body 44. The body 44 is coated with a PTFE (Poly Teflon Fluorine Ethylene) material with a good hydrophilicity and high insulating properties, and a low frictional force in a thickness of approximately 10 μm. The tapered portion 42 with about 0.01 inch in length and the sacrificial link 43 with about 0.008 inch or 0.01 inch in length is exposed without an insulating coating so that it can be dissolved in electrolysis. Referring to FIGS. 7A to 7E, there are shown pictorial views of various guiding wires in accordance with a preferred embodiment of the present invention. As shown in FIG. 7, the body 44 is tapered in different fashions toward the sacrificial link 43 to allow it to be easily inserted within the micro catheter 10 and to be adaptively transformed according to a shape of blood vessel.

As mentioned above, in accordance with the assembly of the present invention, the guiding wire 41 does not require a support coil that was provided in the prior art for providing column strength to the guiding wire, thereby making it possible to simplify the structure of the assembly.

In accordance with a preferred embodiment of the present invention, as shown in FIG. 8, a micro-tube 46 may be provided over the connection portion 40. Specifically, the micro-tube 46 is made of pure radiopaque platinum with about 15 μm in thickness and about 0.3–0.5 mm in length, and may be narrowed in the direction of the wire. The micro-tube 46 helps the embolic material to smoothly exit from the distal end of the micro catheter 10. In addition, the micro-envelope 46 made of pure radiopaque platinum functions as a marker for the position of the embolic material in fluoroscopy.

FIG. 9 is a block diagram of an embolic material detachment detecting system in accordance with another preferred embodiment of the present invention.

As shown in FIG. 9, the embolic material detachment detecting system 500 of the present invention comprises a display 60, function keys 70, a micro-controller unit (MCU) 80, a constant current source 90, a current-sensing block 100 and a voltage-sensing block 110. The system 500 incorporates power source such as a battery (not shown) of DC 9V power supply. The function keys 70 and the display 60 are respectively used to set and display current and voltages and an electrolysis time. The constant current source 90 is a typical circuit that generates 2 mA constant current to a patient 130 through a relay 120 under the control of a reference current $C_{ref}$ and the MCU 80.

An insertion process of the inventive assembly into the patient is similar to a conventional described with reference to FIG. 2, and therefore further description thereof is omitted.

First, in order to electrically detach the embolic material 45 positioned within a vascular malformation such as aneurysm from the guiding wire 41, the positive electrode of the power supply (not shown) is attached to the proximal end of the guiding wire 41 and the negative electrode is placed in electrical contact with the skin of the patient 130. In this situation, the constant current of 1~2 mA is applied to the patient 130. Specifically, when the power supply is turned on, the relay 120 is rendered conductive in response to an enable signal RES provided thereto from the MCU 80, resulting in a closed loop including the system 500 and the patient 130. That is, the positive current, which is applied to the guiding wire 41 coupled with the relay 120, flows to the embolic material 45 and the platinum-based wire 31 inserted therein via the sacrificial link 43.

The current-sensing block 100 continuously senses a current across a resistor R and provides a sensed current to the MCU 80. In response to the sensed current from the current-sensing block 100, the MCU 80 provides a current level control signal C to the constant current source 90 so as to allow it to continuously generate the constant current of 1~2 mA.

When the relay 120 is in the conductive state, the voltage-sensing block 110 continuously senses fluctuation in impedance of the sacrificial link 43 by detecting a difference in voltage between nodes A and B in FIG. 9. A sensed voltage by the voltage-sensing block 110, i.e., an impedance value, is forwarded to the MCU 80. Specifically, if the 1~2 mA constant current is provided to the sacrificial link 43 in- the patient 130 for a predefined time period, a minute electrolysis occurs at the embolic material 45 made of iridium (or tungsten) alloy with the main part of platinum, but the majority occurs at the sacrificial link 43 on which no insulating material is coated. In such event, the voltage-sensing block 110 senses minute change in the DC impedance of the distal end of the guiding wire 41 and provides it to the MCU 80.

The MCU 80 determines whether or not the sacrificial link 43 has been disconnected from the guiding wire 41, based on the sensed current value received from the current-sensing block 100 and the impedance change received from the voltage-sensing block 110. After the sacrificial link 43 is disconnected, the MCU 80 activates an alerting device such as a beeper (not shown) to inform the operator of the detachment of the sacrificial link 43. Simultaneously, the MCU 80 renders the relay 120 non-conductive to prevent an unwanted current from being applied to the patient 130, and renders the constant current source 90 non-operative. The MCU 80 also displays on the display 60-current and voltages detected at the moment of detachment. FIG. 10 is a detailed block diagram of the constant current source, the current-sensing block and the voltage-sensing block shown in FIG. 9.

As stated above, in response to the enable signal $R_{ES}$ from the MCU 80, the relay 120 is rendered conductive to form an electrical connection between the patient 130 and the system 500 of the present invention. As shown in FIG. 10, the constant current source 90 includes a digital to analog converter (DAC) 90a, an OP Amp 90b, registers R1 and R2, a transistor Q 90c and a comparator C1 90d. The constant current source 90 provides the 1~2 mA constant current during the operation, based on the reference current $C_{ref}$ and a current signal from a power supply (not shown). The constant current source 90 allows the current applied to the patient 130 to be increased after a delay as shown in FIG. 11, thereby making it possible to protect the patient 130 by avoiding a sudden current application, which could cause an electrical shock. The current-sensing block 100 senses the current across the resistor R by using a comparator C2 100a and generates a sensed current I.

Applying the current, an electrolytic action occurs at the embolic material 45 and the sacrificial link 43 of the guiding wire 41 inserted in the vascular malformation 11. As is well known, a minute electrolysis occurs with platinum with no chemical reaction, but stainless steel is subject to electrolysis. Specifically, since the impedance Z1 of the stainless steel-based sacrificial link 43 (including the tapered portion 42) is less than about 1 kΩ, and the impedance Z2 of the platinum-based embolic material 45 is larger than about 2 kΩ, the majority of current flows across the sacrificial link 43, as indicated by a solid line in FIG. 12. Accordingly, a difference in voltage between the nodes A and B nearly corresponds to the impedance change of the sacrificial link 43, so that it is possible to exactly determine the instant the sacrificial link 43 is detached.

When the relay 120 is in an conductive state, i.e., an electrical connection is formed between the patient 130 and the system 500, the voltage in the node A may be determined by the impedance of the sacrificial link 43. The voltage-sensing block 110 senses the voltage at the node A and analog to digital converter (ADC) in MCU 80 senses the voltage V.

FIG. 13 is a flow chart, which will be used to describe a method for detecting the detachment of an embolic material, in accordance with still another preferred embodiment of the present invention. FIG. 14 is a graphical representation illustrating a change in the voltage of the sacrificial link during electrolysis.

In the following, the inventive method will be described in detail in conjunction with FIGS. 9, and 11 to 14.

At step S1, the embolic material detachment detecting system 500 of the present invention is initialized. Next, the relay 120 is activated at step S2. As mentioned above, the conductive state of the relay 120 forms a closed loop consisting of the system 500 and the patient 130. In FIG. 11, t1 represents the time at which current power is applied to the guiding wire inside the patient 130, and α represents a unique current value of the patient at the time t1. The current value is gradually increased up to 1~2 mA for a predetermined time period (i.e., t1 to t2), as shown in FIG. 11.

Once power is applied to the guiding wire, the voltage between the proximal end of the guiding wire and the body of the patient or the ground is measured for a plurality of times, 10 times per second for example. Likewise the current flowing to the guiding wire is measured for the same number of times.

At step S7, the average Ia of the current measurements and the average Va of the voltage measurements are respectively computed and stored in the memory 140. This average taking would be performed for another set of a plurality of measurements until the following steps verify the detachment of embolic material.

At step S8, the voltage average Va obtained at step S7 is compared with the minimum average Vmin. Here the minimum average is the smallest of all the averages of sets of measurements so far taken, excluding the present average voltage. If the present average voltage is smaller than the minimum average, it is replaced with the present average voltage before the next step S10 is performed. In other words, the present average voltage becomes the minimum average Vmin from perspective of the next cycle of voltage measurements. At step S10, a fluctuation in the impedance of the sa crificial link 43 is calculated based on the minimum voltag e Vmin, the present average voltage Va and the present aver age current Ia by using the following equations.

$$Fv = \frac{Va - Vmin}{Ia} \quad \text{Eq. (1)}$$

$$Fs = \frac{Va - Vp}{Ia} \quad \text{Eq. (2)}$$

wherein, Fv and Fs represent a fluctuation in the impedance of the sacrificial link, respectively, and Vp represents the average of the previous measurements of voltage.

After the impedance fluctuation by using the above Eqs. (1) and (2) is calculated, the present average Va would be stored as the previous average Vp ("previous" from the perspective of the next average voltage of new voltage measurements). At step S11, if Fv is greater than a first predetermined threshold or Fs is greater than a second predetermined threshold, it is determined that the sacrificial link 43 has been detached. Then the relay 120 is turned off to a non-conductive state. Otherwise, another plurality of measurements is taken to compute new present average voltage and current. More specifically at step S11, in case that the first and second predetermined thresholds are e.g., 0.4 and 0.3, respectively, a relation Fv>0.4 represents that the sacrificial link 43 has been gradually broken, and a relation Fs>0.3 represents that the sacrificial link 43 has been suddenly broken. For example, FIG. 11 represents an illustrative case that the sacrificial link 43 has been suddenly detached, which shows that the sacrificial link 43 begins to be electrolyzed at time t3 and is detached at time t4. In short, the total time taken to electrolyze the sacrificial link 43 is from t1 to t4 and the total time taken for the disappearance of the sacrificial link 43 is from t3 to t4.

FIGS. 15A and 15B are various types of tubes used in keeping therein an assembly for embolization with the embolic material 45 and the guiding wire 41, in accordance with a preferred embodiment of the present invention.

As shown in FIG. 15A, a tube 140 is tailored to have a length and an internal diameter sufficient to keep the assembly therein and is rolled in a preset diameter. The tube 140 is made of polyethylene. A multiplicity of clips 141 is also disposed at certain intervals on the rolled tube 140 to maintain the rolling. The multiplicity of the clips 141 is designed in a one side-opened form to permit the tube 140 to be plucked out of them.

As shown in FIG. 15A, the tube 140 is rolled such that two ends are on a substantially straight line. It allows the insertion of the embolic material 45 into the vascular malformation 11 rather easy. That is, the operator aligns the outlet end of the rolled tube 140 to the implant of a micro catheter 10, and holds and pushes the guiding wire at the side of the implant end of the tube so that the outlet end of the guiding wire is inserted into the implant of the micro catheter 10 toward the vascular malformation 11.

FIG. 15B is a pictorial view depicting clips. As shown in FIG. 15C, the tube 150 may be concentrically rolled using the clips of FIG. 15B.

As previously mentioned, the present invention employs an embolic material into which a platinum wire with a good conductivity is inserted to thereby enhance a column strength of the embolic material and effectively increase a thrombus rate without any application of a high power to the material.

Furthermore, the present invention employs a guiding member having various tapered portions thereon and a specific tailored tube for housing therein the guiding member and the embolic material, to allow the embolic material to be easily inserted into a vascular malformation such as cerebral aneurysms.

Moreover, the present invention employs a micro-envelope tailored to surround a minute stepped portion at which a connection portion and the embolic material are coupled, to thereby allow incoming and outgoing of the embolic material in a distal end of a micro catheter to be easy.

In addition, in contrast with the conventional apparatus using a DC power with AC superposition, the present invention employs a single DC power supply to thereby simplify the structure thereof and lower a production cost.

Likewise, the present invention automatically senses a minute fluctuation in DC impedance in a sacrificial link to thereby exactly detect the instant the embolic material is detached from the guiding member.

While the present invention has been described and illustrated with respect to a preferred embodiment of the invention, it will be apparent to those skilled in the art that variations and modifications are possible without deviating from the broad principles and teachings of the present invention which should be limited solely by the scope of the claims appended hereto.

What is claimed is:

1. A system for detecting the detachment of an implant from a guiding member coupled thereto, wherein the implant is guided by the guiding member into a target site in a living being, comprising:

means for generating a current;

means for supplying the generated current via the guiding member to the implant;

means for measuring a voltage and current between the guiding member and the ground for a plurality of cycles, during each of which the voltage and current are measured for a plurality of times;

means for computing the average of the measured voltages and the average of the measured currents in each cycle;

means for determining the detachment of an implant from the guiding member based on a change in impedance between the guiding member and the ground, wherein the change is detected using the average voltage and average current of the latest cycle of voltage and current measurements, and the average voltage of the previous cycle of voltage and current measurements;

means for extracting the minimum of average voltages each of which is taken for a plurality of voltage measurements; and means for comparing the minimum with the present average, and storing the present average as a new minimum voltage if it is less than the minimum voltage.

2. The system of claim 1, wherein the generated current is a direct current.

3. The system of claim 1, wherein the comparing means includes:

means for calculating a first fluctuation in impedance for the implant according to:

$$Fv = \frac{Va - Vmin}{Ia}$$

wherein Vmin, Va and Ia represent the minimum voltage, the present average of the measured voltages and the present average of the measured currents, respectively; and a first estimation means for comparing the first impedance fluctuation to a first predefined threshold, and determining that the implant has been suddenly detached from the guiding member, if the first impedance fluctuation is larger than the first predefined threshold.

4. The system of claim 3, wherein the comparing means further includes:

means for computing a second fluctuation in impedance for the implant according to:

$$Fs = \frac{Va - Vp}{Ia}$$

wherein Va, Vp and Ia represent the present average of the measured voltages, the previous average voltage and the present average of the measured currents, respectively; and a second estimation means for comparing the second impedance fluctuation and a second predefined threshold, and determining that the implant has been gradually detached from the guiding member, if the second impedance fluctuation is larger than the second predefined threshold.

5. The system of claims 3 or 4, wherein the comparing means further includes means for updating the present average as a new previous average voltage.

6. The system of claim 1, wherein the implant includes an electrically conducting wire which is passed there through.

7. The system of claim 6, wherein the distal end of the guiding member has an external diameter smaller slightly than the internal diameter of the implant and is connected to the electrically conducting wire within the implant by welding.

8. A method for detecting the detachment of an implant from a guiding member coupled thereto, wherein the implant is guided by the guiding member into a target site in a living being, comprising the steps of:

(a) generating a current;

(b) supplying the generated current via the guiding member to the implant;

(c) repeatedly measuring a voltage and current between the guiding member and the ground for a plurality of cycles, during each of which the voltage and current are measured for a plurality of times;

(d) computing an average of the measured voltages and an average of the measured currents in each cycle;

(e) determining the detachment of an implant from the guiding member based on a change in impedance between the guiding member and the ground, wherein the change is detected using the average voltage and average current of the latest cycle of voltage and current measurements, and the average voltage of the previous cycle of voltage and current measurements;

(f) extracting the minimum of average voltages each of which is taken for a plurality of voltage measurements; and (g) comparing the minimum and the present average, and storing the present average as a new minimum if it is less than the minimum.

9. The method of claim 8, wherein the generated current is a direct current.

10. The method of claim 8, wherein the step (g) includes the steps of:

(g1) calculating a first fluctuation in impedance for the implant according to:

$$Fv = \frac{Va - Vmin}{Ia}$$

wherein Vmin, Va and Ia represent the minimum voltage, the present average of the measured voltages and the present average of the measured currents, respectively; and (g2) comparing the first impedance fluctuation and a first predefined threshold, and determining that the implant has been suddenly detached from the guiding member, if the first impedance fluctuation is larger than the first predefined threshold.

11. The method of claim 10, wherein the step (g) further includes the steps of:

(g3) computing a second fluctuation in impedance for the implant according to:

$$Fs = \frac{Va - Vp}{Ia}$$

wherein Va, Vp and Ia represent the present average of the measured voltages, the previous average voltage and the present average of the measured currents, respectively; and (g4) comparing the second impedance fluctuation and a second predefined threshold, and determining that the implant has been gradually detached from the guiding member, if the second impedance fluctuation. is larger than the second predefined threshold.

12. The method of claims 10 or 11, wherein the step (g) further includes the step of updating the present average of the measured voltages as a new previous average voltage.

13. The method of claim 8, wherein the implant includes an electrically conducting wire which is passed there through.

14. The method of claim 13, wherein the distal end of the guiding member has an external diameter smaller slightly than an internal diameter of the implant and is connected with the electrically conducting wire within the implant by welding.

* * * * *